United States Patent
Altmann et al.

(10) Patent No.: US 9,322,715 B2
(45) Date of Patent: *Apr. 26, 2016

(54) THREE-DIMENSIONAL HOT SPOT LOCALIZATION

(71) Applicants: DCG Systems, Inc., Fremont, CA (US); Fraunhofer-Gesellschaft zur Förderung der angewandten Forschung e.V., München (DE)

(72) Inventors: Frank Altmann, Halle (DE); Christian Schmidt, Halle (DE); Rudolf Schlangen, San Francisco, CA (US); Herve Deslandes, Sunnyvale, CA (US)

(73) Assignees: DCG SYSTEMS, INC., Fremont, CA (US); FRAUNHOFER-GESELLSCHAFT ZUR FÖRDERUNG DER ANGEWANDTEN FORSCHUNG E.V., München (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/294,016

(22) Filed: Jun. 2, 2014

(65) Prior Publication Data
US 2014/0346360 A1    Nov. 27, 2014

Related U.S. Application Data

(62) Division of application No. 13/156,289, filed on Jun. 8, 2011, now Pat. No. 8,742,347.

(60) Provisional application No. 61/352,738, filed on Jun. 8, 2010.

(51) Int. Cl.
*G01J 5/00* (2006.01)
*G01R 31/311* (2006.01)
(Continued)

(52) U.S. Cl.
CPC ............ *G01J 5/0066* (2013.01); *G01N 1/00* (2013.01); *G01N 21/88* (2013.01); *G01N 25/00* (2013.01);
(Continued)

(58) Field of Classification Search
CPC ..... G01N 25/72; G01N 25/00; G01N 29/228; G01N 21/71; G01N 2203/0694; G01N 25/18; G01N 21/314; G01N 21/35; G01N 21/359; G01N 1/00

USPC .......................................................... 250/332
See application file for complete search history.

(56) References Cited

U.S. PATENT DOCUMENTS 4,557,607 A    12/1985    Busse
4,950,897 A    8/1990    Mandelis et al.
(Continued)

FOREIGN PATENT DOCUMENTS

CN    1696674 A    11/2005
CN    103026216 A    4/2013
(Continued)

OTHER PUBLICATIONS

Altmann, F. et al., "Characterization and Failure Analysis of 3D Integrated Semiconductor Devices-Novel Tools for Fault Isolation, Target Preparation and High Resolution Material Analysis," ISTFA 2010: Proceedings of the 36th International Symposium for Testing and Failure Analysis (ASM International), Fraunhofer Institute for Mechanics of Materials, Halle, Germany, Nov. 1, 2010, pp. 163-170.
(Continued)

*Primary Examiner* — Marcus Taningco
(74) *Attorney, Agent, or Firm* — Nixon Peabody LLP; Joseph Bach, Esq.

(57) ABSTRACT

A non-destructive approach for the 3D localization of buried hot spots in electronic device architectures by use of Lock-in Thermography (LIT). The 3D analysis is based on the principles of thermal wave propagation through different material layers and the resulting phase shift/thermal time delay. With more complex multi level stacked die architectures it is necessary to acquire multiple LIT results at different excitation frequencies for precise hot spot depth localization. Additionally, the use of multiple time-resolved thermal waveforms, measured in a minimized field of view on top of the hot spot location, can be used to speed up the data acquisition. The shape of the resulting waveforms can be analyzed to further increase the detection accuracy and confidence level.

20 Claims, 6 Drawing Sheets

(51) Int. Cl.
*G01N 1/00* (2006.01)
*G01N 25/00* (2006.01)
*G01N 21/88* (2006.01)
*G01N 21/35* (2014.01)
*G01N 21/84* (2006.01)

(52) U.S. Cl.
CPC ....... *G01R 31/311* (2013.01); *G01J 2005/0077* (2013.01); *G01J 2005/0085* (2013.01); *G01N 21/35* (2013.01); *G01N 2021/8461* (2013.01)

(56) References Cited

U.S. PATENT DOCUMENTS

| | | | |
|---|---|---|---|
| 5,667,300 | A | 9/1997 | Mandelis et al. |
| 6,399,948 | B1 | 6/2002 | Thomas et al. |
| 6,759,659 | B2 | 7/2004 | Thomas et al. |
| 6,786,098 | B2 | 9/2004 | Bates |
| 6,812,468 | B1 | 11/2004 | Baumann et al. |
| 6,840,667 | B2 | 1/2005 | Schlagheck et al. |
| 7,018,094 | B1 | 3/2006 | Bates |
| 7,131,331 | B2 | 11/2006 | Bates |
| 7,272,207 | B1* | 9/2007 | Aufrichtig et al. ............ 378/116 |
| 7,429,735 | B2 | 9/2008 | Lueerssen et al. |
| 7,444,260 | B2 | 10/2008 | Raad |
| 7,554,086 | B2 | 6/2009 | Shepard et al. |
| 7,709,794 | B2 | 5/2010 | Zhao et al. |
| 8,306,608 | B2 | 11/2012 | Mandelis et al. |
| 8,742,347 | B2 | 6/2014 | Altmann et al. |
| 9,025,020 | B2 | 5/2015 | Deslandes et al. |
| 9,098,892 | B2 | 8/2015 | Deslandes et al. |
| 2002/0172410 | A1 | 11/2002 | Shepard |
| 2003/0137318 | A1 | 7/2003 | Enachescu et al. |
| 2005/0008215 | A1 | 1/2005 | Shepard |
| 2005/0056786 | A1 | 3/2005 | Shepard et al. |
| 2006/0140445 | A1 | 6/2006 | Cusack |
| 2007/0021670 | A1 | 1/2007 | Mandelis et al. |
| 2009/0201971 | A1 | 8/2009 | Goldammer et al. |
| 2009/0245322 | A1 | 10/2009 | Hudgings et al. |
| 2009/0297017 | A1 | 12/2009 | Hudgings et al. |
| 2010/0062550 | A1 | 3/2010 | Buchel et al. |
| 2010/0073665 | A1* | 3/2010 | Zhao et al. ...................... 356/36 |
| 2010/0074515 | A1 | 3/2010 | Zhao et al. |
| 2010/0091812 | A1 | 4/2010 | Louban et al. |
| 2010/0163732 | A1 | 7/2010 | Louban et al. |
| 2011/0297829 | A1 | 12/2011 | Altmann et al. |
| 2012/0098957 | A1 | 4/2012 | Deslandes et al. |
| 2014/0210994 | A1 | 7/2014 | Deslandes et al. |

FOREIGN PATENT DOCUMENTS

| | | |
|---|---|---|
| DE | 4203272 A1 | 8/1993 |
| DE | 19838858 A1 | 4/1999 |
| DE | 19835616 A1 | 2/2000 |
| DE | 19835616 C2 | 2/2002 |
| DE | 10053112 A1 | 5/2002 |
| DE | 10059854 A1 | 6/2002 |
| DE | 10150633 A1 | 4/2003 |
| DE | 60016939 T2 | 12/2005 |
| DE | 10 2005 053 203 A1 | 5/2007 |
| DE | 10 2006 043 339 A1 | 3/2008 |
| DE | 10 2007 037 377 A1 | 2/2009 |
| DE | 10 2007 058 566 A1 | 6/2009 |
| EP | 1 852 697 A1 | 11/2007 |
| EP | 2 444 795 A1 | 4/2012 |
| EP | 2 580 583 A1 | 4/2013 |
| JP | 07-92237 A | 4/1995 |
| JP | 09-505886 A | 6/1997 |
| JP | 2004-069439 A | 3/2004 |
| JP | 2008-16778 A | 1/2008 |
| JP | 2009-511876 A | 3/2009 |
| JP | 2012-093355 A | 5/2012 |
| JP | 2013-526723 A | 6/2013 |
| JP | 5631484 B2 | 10/2014 |
| JP | 2014-222243 A | 11/2014 |
| KR | 2013-0087487 A | 8/2013 |
| SG | 180133 A1 | 5/2012 |
| SG | 186207 A1 | 1/2013 |
| TW | 201215881 A1 | 4/2012 |
| TW | 201229504 A1 | 7/2012 |
| TW | I460422 B | 11/2014 |
| TW | I468677 B | 1/2015 |
| WO | 01/29545 A1 | 4/2001 |
| WO | 2007/147158 A2 | 12/2007 |
| WO | 2010/099964 A3 | 9/2010 |
| WO | 2011/156527 A1 | 12/2011 |

OTHER PUBLICATIONS

Breitenstein, O. et al., Lock-in Thermography: Basics and Use for Evaluating Electronic Devices and Materials Series, Springer Series in Advanced Microelectronics, vol. 10, 2nd ed., 2010, X, 258 pages.

Breitenstein, O., et al., "Unusual Lock-In Thermography Signals: Schottky-Type Grid Contacts, Peltier Effects, and Thermal Wave Interference," IV World Conference on Photovoltaic Energy Conversion, May 7-12, 2006, Waikaloa, Hawaii, pp. 912-915.

Dillenz, A., "Progress in Phase Angle Thermography," Review of Scientific Instruments, AIP, Melville, NY, US, vol. 74, No. 1, Jan. 1, 2003, pp. 417-419.

Dorr, P., "Multi-Parameter-Fitting Procedure for Photothermal Infrared Radiometry on Multilayered and Bulk-Absorbing Solids," Journal of Applied Physics, American Institute of Physics, New York, US, vol. 89, No. 12, Jun. 15, 2001, pp. 7888-7894.

Junyan, L., "Research on Thermal Wave Processing of Lock-in Thermography Based on Analyzing Image Sequences for NDT," Infrared Physics & Technology, Elsevier Science B.V. Netherlands, vol. 53, No. 5, Sep. 2010, pp. 348-357.

Liu, H. et al., "Effect of Modulation Frequency on Detecting Defects of Metal Plates Using Infrared Lock-in Thermography," Proceedings of SPIE—The International Society for Optical Engineering—4th International Symposium on Advanced Optical Manufacturing and Testing Technologies: Optical Test and Measurement Technology and Equipment 2009 SPIE USA, vol. 7283, Nov. 19, 2008, pp. 72833M-1 to 72833M-7.

Maldague, X., "Active Thermography," Theory and Practice of Infrared Technology for Nondestructive Testing, Wiley, John & Sons, Incorporated, Chapter 9, Apr. 2001, pp. 343-365.

Schmidt, C., et al., "Application of Lock-in-Thermography for 3D Defect Localisation in Complex Devices", 2nd Electronics Systemintegration Technology Conference, 2008. 2nd IEEE, Piscataway, NJ, USA, Sep. 1, 2008, pp. 1041-1044.

Schmidt, C., "Localization of Electrical Defects in System in Package Devices Using Lock-in Thermography", Electronic System-Integration Technology Conference (ESTC), 2010 3RD, IEEE, Piscataway, NJ, USA, Sep. 13, 2010, pp. 1-5.

Schmidt, C. et al., "Lock-in-Thermography for 3-Dimensional Localization of Electrical Defects Inside Complex Packaged Devices", Conference Proceedings from the International Symposium for Testing and Failure Analysis (34th International Symposium for Testing and Failure Analysis, ISTFA) Nov. 2-6, 2008, Jan. 1, 2008, pp. 102-107.

Schmidt, C. et al., "Non-Destructive Defect Depth Determination at Fully Packaged and Stacked Die Devices Using Lock-in Thermography", Physical and Failure Analysis of Integrated Circuits (IPFA), 2010, 17th IEEE International Symposium, IEEE, Piscataway, NJ, USA, Jul. 5, 2010, pp. 1-5.

Schmidt, C. et al., "Thermal Simulation of Defect Localization Using Lock-In Thermography in Complex and Fully Packaged Devices," Thermal, Mechanical and Multi-Physics Simulation and Experiments in Microelectronics and Microsystems, 2009, Eurosime 2009, 10th International Conference on, IEEE, Piscataway, NJ, USA, Apr. 26, 2009, pp. 1-7.

Tarin, M. et al., "Fuselage Inspection of Boeing-737 Using Lock-in Thermography," The International Society for Optical Engineering SPIE, Proceedings of the SPIE—Thermosense XXX, Mar. 18-20, 2008, Orlando, FL, USA, vol. 6939, pp. 693919-1 to 693919-10.

(56) References Cited

OTHER PUBLICATIONS

"Heat Flux Thermography: From Laboratory System to Industrial Application," Thermosensorik GmbH, Germany, May 1, 2009, Inspect-Online, available at http://www.inspect-online.com/en/topstories/control/heat-flux-thermography, retrieved Oct. 11, 2011.
Office Action in U.S. Appl. No. 13/156,289, mailed on Aug. 24, 2012.
Office Action in U.S. Appl. No. 13/156,289, mailed on Apr. 3, 2013.
Notice of Allowance in U.S. Appl. No. 13/156,289, mailed on Jan. 16, 2014.
Office Action in U.S. Appl. No. 13/280,260, mailed on Dec. 27, 2013.
Office Action in U.S. Appl. No. 13/280,260, mailed on Jun. 16, 2014.
Extended European Search Report in European Application No. 11185795.9, mailed on Feb. 17, 2012.
Examination Report in European Patent Application No. 11185795.9, dated Jun. 16, 2014.
First Office Action for Chinese Patent Application No. 201180036274.0, dated Mar. 4, 2014.
Office Action in Japanese Patent Application No. 2013-512069, dated Nov. 5, 2013.
Notice of Decision of Refusal for Japanese Patent Application No. 2013-512069, dated Mar. 28, 2014.
Notice of Decision to Grant Japanese Patent Application No. 2013-512069, dated Sep. 30, 2014.
Examination and Search Report in Taiwanese Patent Application No. 100119928, mailed on Apr. 15, 2014.
Examination Report in Taiwanese Patent Application No. 100137995, mailed on Apr. 22, 2014.
PCT International Search Report and Written Opinion in International Application No. PCT/US2011/039679, mailed on Sep. 20, 2011.
PCT International Preliminary Report on Patentability in International Application No. PCT/US2011/039679, mailed on Dec. 20, 2012.
PCT International Search Report and Written Opinion in International Application No. PCT/EP2012/074982, mailed on Apr. 8, 2013.
Notice of Allowance in U.S. Appl. No. 13/280,260 dated Jan. 2, 2015.
Second Office Action for Chinese Patent Application No. 201180036274.0, dated Nov. 25, 2014.
Notice of Allowance of Taiwanese Patent Application No. 100119928 dated Sep. 24, 2014.
Notice of Allowance of Taiwanese Patent Application No. 100137995 dated Jul. 30, 2014.
Third Office Action for Chinese Patent Application No. 201180036274.0, dated Jun. 9, 2015.
Office Action for Japanese Patent Application No. 2014-148290 dated Jul. 28, 2015.
Office Action for Japanese Patent Application No. 2011-233006 dated Jul. 28, 2015.
Notice of Allowance for U.S. Appl. No. 14/243,859 dated Mar. 27, 2015.
Fourth Office Action for Chinese Patent Application No. 201180036274.0 dated Dec. 10, 2015.
Search and Examination Report for Singapore Patent Application No. 10201504489T dated Jan. 13, 2016.

\* cited by examiner

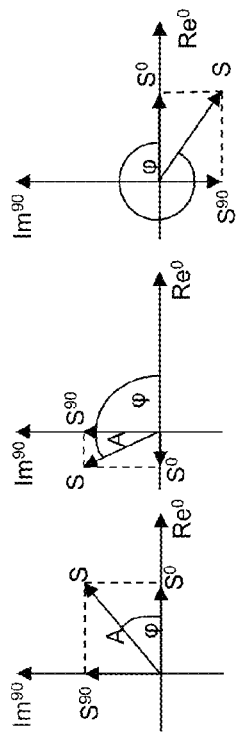
*Figure 1 – Prior Art*
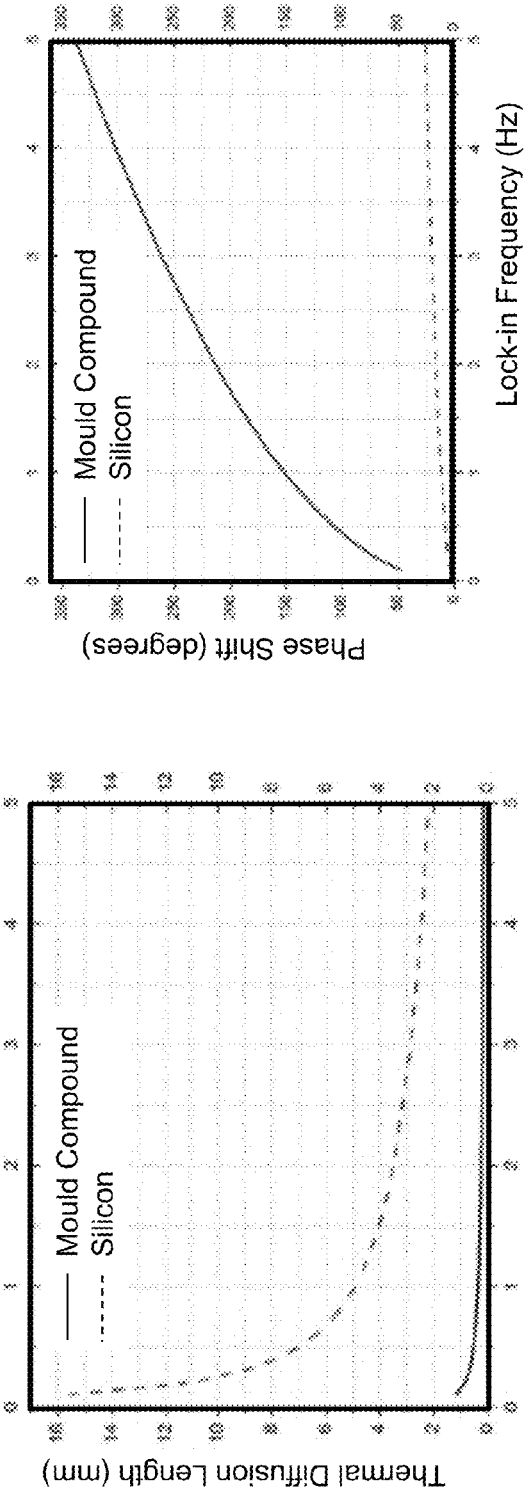
*Figure 3*
*Figure 2*

*Figure 11A (Amplitude)*

*Figure 11B (Phase)*

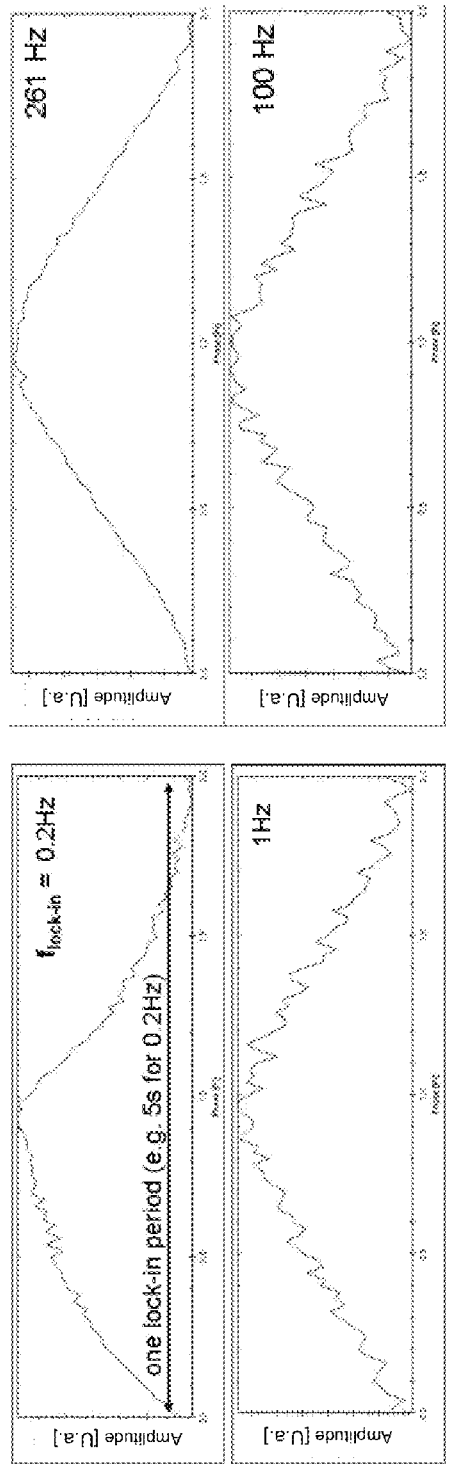
FIGURE 12
FIGURE 13
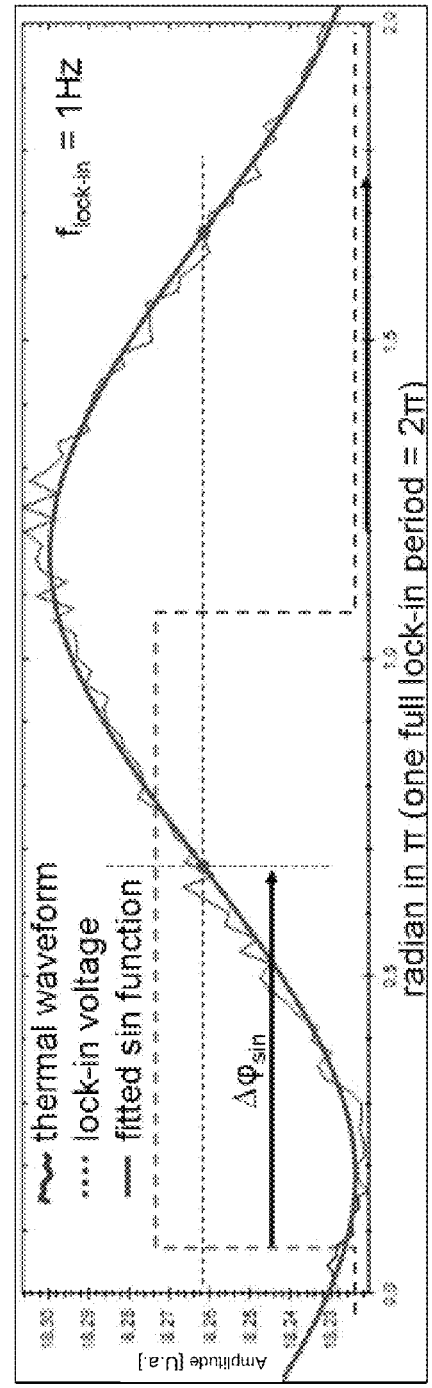
FIGURE 14

THREE-DIMENSIONAL HOT SPOT LOCALIZATION

RELATED APPLICATIONS

This application is a divisional of U.S. application Ser. No. 13/156,289, filed on Jun. 8, 2011, entitled "Three-Dimensional Hot Spot Localization," which claims priority benefit from U.S. Provisional Application Ser. No. 61/352,738, filed on Jun. 8, 2010, the disclosures of which are incorporated herein by reference in their entirety.

BACKGROUND

1. Field of Invention

This invention is in the field of localization of resistive heat sources (hot spots), buried inside of electronic devices. Using the described invention, the positions of hot spots can be located and pinpointed in all three dimensions by analyzing the thermal heat propagation through defect-covering layers utilizing lock in amplified thermal imaging. The invention in particular enables a non destructive 3D localization of thermal active structures or defects in a vertical stack of integrated circuits and interconnect layers within system in package devices (SiP).

2. Related Art

Failure analysis of modern complex system in package devices with a three-dimensional architecture is an increasing challenge. In such devices, several integrated circuit dies are vertically stacked and interconnected by wire bond or through silicon via (TSV) technologies. The access to and analysis of internal electronic structures or interconnects is limited to non destructive techniques, like magnetic microscopy, time domain reflectometry which can be used for signal tracking. Both methods are limited in resolution and the three dimensional positioning of electrical defects are very limited or extensive. Standard failure localization methods like OBIRCH or Emission Microscopy can mostly not be applied since the optical access to buried electronic structures within the 3D architecture is limited by opaque material layers. This is most critical in case of 3D system in package devices due to the fact that thermal active structures and defects can be buried at deeper dies or interconnect levels covered by opaque die attach, redistribution or encapsulation layers. Separation of individual dies for separate failure analysis may be an option to localize defects but this process is very time consuming and can come with a high risk of creating additional preparation-related defects reducing significantly the failure analysis success rate.

Current localization techniques of thermal defects which can be electrically stimulated include the following:

Lock In Thermography (LIT)

LIT refers to a non destructive technique that detect very small temperature variations across a sample by direct thermal imaging, using an IR sensitive camera combined with pixel-wise two channel lock in correlation. LIT provides μm spatial resolution and μK sensitivity to locate thermal active structures and defects in x and y coordinates, but until now doesn't enable depth localization.

Depth of Hot Spots within or Under a Material Layer with Homogeneous Thermal Properties For a given thermal homogeneous material there is an approximately linear dependence between the depth of a heat source underneath the surface and the time it takes the heat to reach the surface. This thermal time delay is proportional to the phase signal and can be measured by two channel lock-in thermography, which allows a recalculation of the heat source distance to the surface and therefore its depth within or under the material layer.

Thermal Scope

Conventional time-resolved temperature measurements allow to detect/display the thermal response of a sample with microsecond (μs) and milli-Kelvin (mK) accuracy.

Thermal Pulse Absorption Analysis

Based on pulsing heat onto a surface (backside or frontside) and measuring the temperature distribution/spreading in a time-resolved way. The Pulse Phase Thermography can detect sub-surface delaminations, material impurities, voids, etc. It can be used for contactless detection of weak welding joints (see, e.g., Thermosensorik, of Germany). In comparison to LIT, thermal pulse absorption is less sensitive and provides less spatial resolution.

SUMMARY

The following summary of the disclosure is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

A new approach for localization of heat sources in a non-destructive way by using Lock-in Thermography (LIT) is disclosed. The method of LIT is a very sensitive and easy to handle for hot spot detection and can be applied for the localization of die and packaging level defects. For quantitative LIT analysis and three dimensional allocation of buried heat sources, the basic principles of heat wave propagation, dependence of the thermal and geometrical properties of the material layer above the hot spot area, have to be understood.

Aspects of the invention provide three-dimensional allocation of buried hot spots based on phase and time-resolved thermal response measurements by means of lock-in thermography. A method is disclosed to discriminate one, or multiple thermal active structures, which can be stimulated by applying an electrical signal, out of numerous stacked layers by means of non-destructive measurements of the heat, generated at the thermal active structure inside of the stack and detected on the surface of the device.

The combination of Lock-in Thermography (fast localization of the hot spots in x and y) with time-resolved thermal response measurements at different excitation frequencies (for localization of the hot spots in the z direction) allows fast and secure detection of the thermally active structure.

In addition to the non-destructive localization of thermal heat sources in x and y inside of fully packaged electronic devices, embodiments of this invention allow localizing the defective layer (die) through the encapsulation (including the full layer stack) by measuring and analyzing the phase shifts (in case of Lock-in Thermography) and/or the thermal time delays (in case of time-resolved thermal response measurements) as a function of the applied excitation frequency (lock-in frequency).

While embodiments of the invention are described herein with respect to encapsulated integrated circuits, the invention can also be implemented for testing other devices that generate hot spots by electrical stimulation, such as batteries, solar cells, power devices, LED's, etc. Therefore, the term DUT may be applicable to these devices as well. According to embodiments of the invention, a method is provided for detecting the location of heat sources buried within a sample by using Lock-in Thermography, comprising: placing the sample on a test system; applying test signals to the sample at multiple different lock-in frequencies; while the test signals are applied to the sample, imaging the sample using an infrared sensor; detecting from the imaging lateral temperature distribution on a surface of the sample; detecting and analyzing a resulting phase shift between the test signals and thermal response obtained from the imaging in correlation to thermal heat propagation within the sample; analyzing the lateral temperature distribution to thereby obtain lateral location of the heat sources; and, analyzing the phase shift at each heat source position to thereby determine its depth location within the sample. According to embodiment of the invention, the method further comprises plotting the phase shift at various lock-in frequencies and analyzing the slope of the plotted phase vs. frequency curve in addition to the quantitative phase values to improve depth resolution and measurement reliability. The analysis may include calculating depth related phase shift to frequency behavior by analytical solution of the thermal wave propagation; and, correlating the calculated depth related phase shift to frequency behavior to the detected phase shift to identify the depth of the heat source. The analysis may also include calculating depth-related phase shift to frequency behavior by finite element modeling of thermal wave propagation; and, correlating the calculated depth-related phase shift to frequency behavior to the detected phase shift to identify the depth of the heat source.

According to embodiments of the invention, a method is provided for detecting the location of heat sources buried within a sample by using Lock-in Thermography, comprising: placing the sample on a test system; applying test signals to the sample; while the test signals are applied to the sample, imaging the sample using an infrared sensor; detecting from the imaging lateral temperature distribution on a surface of the sample and analyzing the lateral temperature distribution to thereby obtain lateral location of the heat sources; Characterized in that: the test signals are applied at multiple different lock-in frequencies; and further by detecting and analyzing a resulting phase shift between the test signals and thermal response obtained from the imaging in correlation to thermal heat propagation within the sample; and, analyzing the phase shift at each heat source position to thereby determine its depth location within the sample. According to embodiment of the invention, the method further comprises plotting the phase shift at various lock-in frequencies and analyzing the slope of the plotted phase vs. frequency curve in addition to the quantitative phase values to improve depth resolution and measurement reliability.

According to embodiments of the invention, a method for detecting the location of buried heat sources using lock-in-thermography (LIT) system is provided, comprising: placing a device under test (DUT) on a test system; applying an electrical signal of a variable lock-in frequency to the DUT while varying the lock-in frequency of the test signal over time; while the test signal is applied to the DUT, imaging the DUT using an infrared camera; using thermal imaging to detect time-resolved thermal waveforms at the variable lock-in frequency and displaying the time-resolved thermal waveform on a monitor; and, analyzing the time-resolved thermal waveform using a correlation function in order to determine the phase shift between the electrical signal and related thermal waveform.

According to embodiments of the invention, a method is provided for detecting the location of electrical active heat source buried within a sample by using Lock-in Thermography, which applies a concept of windowing for faster signal acquisition, the method comprising: applying electrical excitation signal to the sample; while the test signal is applied to the sample, imaging the sample using an infrared camera; detecting lateral temperature distribution on a surface of the sample to thereby locating the heat-source laterally; reducing the operational area of the IR camera to only image the area where the heat-source was localized, an operation generally referred to as sub-array or windowing, so as to gain increased camera acquisition speed, referred to as frame-rate, wherein reducing the operational area of the IR camera may be done by reading data from only a subset of the pixels of the camera; subsequently applying electrical excitation at multiple different lock-in frequencies to the sample; while the test signals are applied to the sample, imaging the sample using the windowing IR camera; detecting lateral temperature distribution on a surface of the sample; detecting and analyzing a resulting phase shift between the electrical excitation signal and the thermal response in correlation to the thermal heat propagation within the sample; and, analyzing the resulting phase shift to thereby obtain depth location of the electrical active heat source.

According to embodiments of the invention, the method includes using one or multiple correlation functions to quantitatively analyze the shape of the time-resolved thermal waveform, for example but not exclusively, by using auto-correlation or cross-correlation to predefined waveforms like sin, cos, square, shark-fin, exponential charging/discharging curve etc., and generating a matrix of resulting correlation factors vs. lock-in frequency.

According to aspects of the invention, a method for localizing defects in device under test (DUT) is provided, comprising: placing the DUT on a test system; applying a test signal of a variable frequency $f_t$ to the DUT while varying the frequency $f_t$ of the test signal over time; while the test signal is applied to the DUT, imaging the DUT using an infrared camera; determining the phase shift of infrared image of the DUT from the test signal frequency $f_t$; and, correlating the phase shift to depth measurement inside the DUT. Imaging the DUT may be done by operating the infrared camera at frame rate $f_c$ higher than the frequency $f_t$. The frequency $f_c$ may be at least four times the frequency $f_t$. The method may further comprise plotting time-resolved phase shift at various frequencies $f_t$.

According to further aspects of the invention, a method for localizing defects in encapsulated integrated circuit (IC) is provided, comprising: placing the encapsulated IC on a test system; applying a first test signal of a selected frequency $f_0$ to the encapsulated IC; while the first test signal is applied to the IC, obtaining an IR image of the IC; from the IR image selecting an area of interest; reducing the field of view of the infrared camera; applying a set of test signals of variable frequency $f_t$ to the encapsulated IC while varying the frequency $f_t$ of the test signals over time; while the test signals are applied to the IC, imaging the IC using the infrared camera with a reduced field of view; using the imaging to generate a time-resolved thermal waveform; and, using the waveform to determine defect depth within the IC.

BRIEF DESCRIPTION OF THE DRAWINGS

Other aspects and features of the invention would be apparent from the detailed description, which is made with reference to the following drawings. It should be mentioned that the detailed description and the drawings provide various non-limiting examples of various embodiments of the invention, which is defined by the appended claims.

FIG. 1 is a complex vector diagram, showing the basic LIT correlation signals (Real part and imaginary part) and in consequence the resulting amplitude vector and phase shift for an increasing distance of the defect position to the device surface, progressing from left to right.

FIG. 2 is a plot of thermal diffusion length as a function of the applied lock-in frequency for the materials silicon and mould compound.

FIG. 3 is a plot of the resulting phase shift as a function of the applied lock-in frequency resulting from an assumed defect under a one millimeter material layer of silicon and mould compound.

FIG. 11A is a LIT results of overlay of topography and lock-in amplitude image, while FIG. 11B is the phase results.

FIG. 12 is a plot of time-resolved thermal response (similar to thermal waveforms); all measured with $V_{lockin}$=1.2V, time of acquisition=40 sec, at full frame mode of camera (frame rate=100 Hz), for different lock-in frequencies.

FIG. 13 is a plot of time-resolved thermal response (similar to thermal waveforms); all measured with $f_{lockin}$=1 Hz, $V_{lockin}$=1.2V, time of acquisition=40 sec, at different sub frame modes of camera (windowing, with higher frame rates).

FIG. 14 is a plot of time-resolved thermal response, measured with $f_{lockin}$=1 Hz, $V_{lockin}$=1.2V, time of acquisition=40 sec, full frame mode (100 Hz), with an overlay of the excitation/lock-in voltage and a sin function at the delay point of highest cross-correlation. The cross-correlation result can be used to determine the phase shift $\Delta\phi_{sin}$ with increased accuracy.

DETAILED DESCRIPTION

Figure 5:
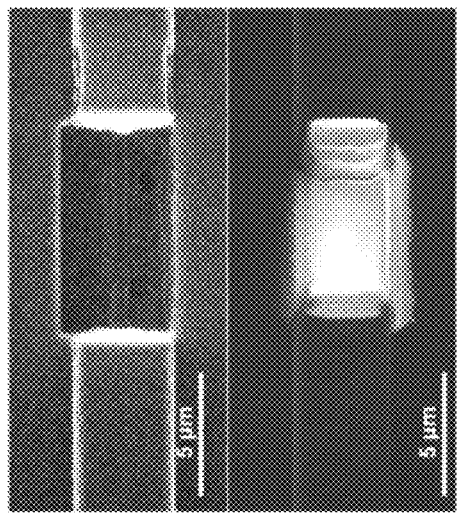
FIG. 5 is an image showing the creation of a localized defect using focused ion beam based circuit editing.

Three dimensional architectures of electronic devices e.g. system in packages (SiP) are composed of several integrated circuit dies, die attaches or interconnect redistribution layers stacked vertically and encapsulated together. Consequently, such encapsulated electronic devices are heterogenous material stacks containing silicon, polymer and Si-oxide isolators, metal lines and wires, glue and/or adhesives, encapsulation mould, etc. Therefore, the internal heat propagation starting from the hot spot position can be very complex. Consequently, location of a hot spot defect in the z direction, i.e., its depth within the sample, is difficult. Furthermore, complex defects or sample types may result in non-ideal hot spot activation in terms of power conversion at the hot spot location. Various embodiments disclosed herein enable accurate localization of heat sources (e.g. thermally active structures or defects) in such devices.

Various embodiments of the invention use defined multiple frequencies for device excitation (primarily, but not exclusively square waves voltage signals with 50% duty cycle). Analysis of the resulting phase shift between excitation and thermal response vs. frequency curve enables the necessary hot spot depth calculation accuracy, including a comparison to simulated and/or pre-calibrated data. Time-resolved thermal response measurements (similar to the display of a thermal scope) are used to analyze the full thermal waveform for better accuracy with strongly reduced analysis time.

Embodiments of the invention use quantitative measures for the phase shift/time delay between electrical stimulation and thermal response and the shape of the measured waveform for automated and semi-automated data analysis. The waveform shape analysis can be based on cross-correlation between the measured results and pre-defined functions (e.g. sine, cosine, shark-fin, triangle, square), delivering a correlation matrix rather than just single phase values per applied lock-in.

The embodiments of the invention provide advantages such as: scanning the lock-in frequency offers measuring more data points and allows analyzing not only the individual absolute phase values, but also the shape/slope of the phase vs. frequency curve. This offers an well-defined phase shift/time delay measurement with increased detection accuracy and still allows 3D localization with non-ideal hot spot activation, where a single phase measurement would deliver wrong results. Also, the time resolved thermal response measurements can substantially reduce the necessary acquisition time per analyzed frequency by more than ten times, and potentially by up to 100 times. Furthermore, the gained full waveform allows further improved depth measurement accuracy, based on the quantitative analysis of the thermal time delay and the waveform shape. These improvements are expected to be necessary to resolve single layers in current and future multi layer electronic devices, i.e. 3D system in package technologies. The quantitative analysis of the thermal heat propagation allows for (semi) automated 3D allocation of hot spots.

The main advantage of LIT in contrast to steady-state Thermography is the much higher sensitivity down to a few µW combined with higher spatial resolution down to a few µm. In order to achieve these parameters the device under test is periodically stimulated with a supply voltage by a chosen frequency (lock-in frequency). The resulting thermal response at the device surface is detected by an IR camera and split into an in-phase-part (S0°) and an out-of phase-part) (S90°) related to the excitation signal by using two correlation functions. This process allows the calculation of amplitude and phase signal, which contain the necessary information for hot spot depth localization.

$$\text{Amplitude } \sqrt{(S^{0°} + S^{90°})^2} \quad (1)$$

$$\text{Phase:} \arctan\frac{S^{90°}}{S^{0°}} \quad (2)$$

For a better understanding of the relation ship between the basic signals (S0°, S90°) and the resulting amplitude and phase information, the 0° and the 90° signals are plotted in a complex vector diagram, shown in FIG. 1. The resulting vector of both parts represents the amplitude A (arrow leading to point "S" in FIG. 1) whereby the angle between 0° and the resulting amplitude vector is represented by the phase ϕ. The phase value can be understood as a time delay between the excitation signal and the measured thermal response.

In general, since the test is performed on devices with a material above the hot spot area is not transparent for the detected IR wavelength (typically but not exclusively 3-5 um) thermal waves can propagate through this material, resulting in a periodically increased temperature at the device surface above the hot spot, which can be measured by LIT. The time constant of the underlying thermal diffusion process determines the phase shift between excitation signal and thermal response. The main contributors to the thermal delay are the material layers with less heat conductivity like mould compound, die attach glues, polymer and Si oxide isolators, but not the Si dies or metal layers which have ha much higher heat conductivity. In simple terms, the longer the distance between hot spot and device surface, the higher the resulting phase shift. Reversely, knowing the thermal properties of the material above the hot spot, allows the determination of an unknown depth of hot spots by measuring the phase shift.

The parameter which describes the influence of the thermal properties of a material layer is herein called thermal diffusion length ($\mu$) which describes the damping of the thermal wave inside the bulk material. It is defined as the characteristic length where the amplitude of the thermal wave is dropped down to $e^{-1}$. It can be calculated, as shown in equation 3, by the thermal parameters heat conductivity ($\lambda$ in W/m*K), specific heat capacity (cp in J/g*K), density ($\rho$ in g/cm$^3$) and the applied lock-in frequency ($f_{lock-in}$ in Hz). The thermal parameters can be summarized as the thermal diffusivity (a in mm$^2$/s).

$$\mu = \sqrt{\frac{2*\lambda}{c_p * \rho * 2\pi f_{lock-in}}} = \sqrt{\frac{2a}{2\pi f_{lock-in}}} \quad (3)$$

The thermal diffusion length $\mu$ (in mm) is characteristic for each material propagated by the thermal wave. FIG. 2 shows the thermal diffusion length of two examples, mould compound (solid line) and silicon (dashed line). It can be observed that the thermal diffusion length of mould compound is significantly shorter compared to silicon. Furthermore it can be seen from FIG. 2 that the lower the applied frequency is, the deeper the thermal wave propagates into the solid material. Consequently, reducing the frequency of the excitation signal allows the localization of heat sources even through hundreds of microns of IR-opaque material layers.

Due to the fact that the thermal diffusion length can be seen as the damping factor to the thermal wave, it affects not only the amplitude but also the resulting phase. A higher lock-in frequency results in a higher time delay between excitation signal at the hot spot position and the thermal response at the device surface. Therefore, an increase of the phase shift as a function of the increased lock-in frequency has to be expected.

The relationship between Phase ϕ and hot spot depth z is described as:

$$\Phi = \frac{z}{\mu} * 180/\pi \quad (4)$$

whereby $\mu$ represents the thermal diffusion length. FIG. 3 is a plot of the resulting phase shift as a function of the applied lock-in frequency for a hot spot buried under a one millimeter material layer. The solid line is a plot for the mould compound while the broken line is for the silicon.

According to one embodiment, the detailed analysis of the internal heat propagation and the separation of different influences to the resulting phase shift is investigated using the method of finite element modelling. The modelling is used to simulate the lock-in process for a known device build up and defined hot spot positions. The heat transfer through a 3D system-in-package device can be done using 2D/3-D thermal modelling. Assuming different heat sources at different lateral and vertical positions inside of the device and correlating the resulting phase shifts for various lock in frequencies to the experimental data enables an identification of internal hot spot positions.

As a first step, the steady state solution that considers the transient response is calculated using half of the assumed dissipation power in order to reach a stable modulation within a few cycles. After reaching this "quasi—steady state," the sample is stimulated with the pulsed excitation signal. Lock-in frequency, number of excitation periods and number of intermediate steps are chosen with reference to the real geometries and thermal parameters (heat conductivity, heat capacity and density). The dissipation power is applied to the model ground and pulsed by various lock in frequencies. In addition, the time and power dissipation signals are saved in separate files, allowing the creation of the correlation functions and the reconstruction of the excitation signal. Two paths are created, where one is reading the temperature modulation over the surface and one over the thickness of the sample.

Figure 4:
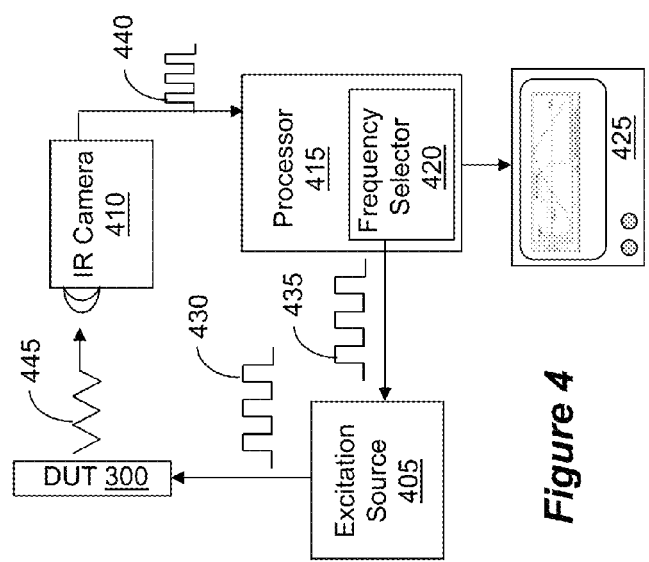
FIG. 4 is a diagram of a system according to an embodiment of the invention.

FIG. 4 is a diagram of a system according to an embodiment of the invention. DUT 400 is stimulated by excitation signal 430 at frequency $f_0$ generated by excitation source 405. In one example the excitation signal 430 is a square wave having amplitude voltage equal to the DUT's operational voltage, e.g., 1.2 V, and a lock-in frequency $f_0$. The frequency $f_0$ of the excitation signal is set and varied by frequency selector part 420, of processor 415. A sync signal 435 is output from the processor 415 and sent to the excitation source 405. The simplest is to set the sync signal 435 at the same frequency $f_0$, although it may be a different frequency, so long as provisions are made to enable excitation source 405 to generate the excitation signal 430 at frequency $f_0$. An IR camera 410 is used to snap IR images of selected area of the DUT 400. The frame rate of camera 410 is usually but not exclusively set to be higher than the frequency $f_0$. Here it is set to at least four times higher than frequency $f_0$. This operation can also be handled by an ATE, i.e., the ATE sends the drive signal to the DUT and at the same time sends a trigger signal to the controller and the camera.

With the setup of FIG. 4, unlike the prior art, the DUT 400 is repeatedly excited by excitation source 405, while the frequency $f_0$ of the excitation signal is varied according to the sync signal 435 provided by the frequency selector 420. This enables a better and more accurate identification of a hot spot's location, especially its depth (i.e. z direction) within the electronic device. Additionally, unlike the prior art, the setup of FIG. 4 does not output a single phase data point, but rather enables plotting the entire response curve on monitor 425. Having the entire response curve enables further analysis, such as curve fitting to better understand the time-resolved heat dissipation within the DUT. Notably, as can be appreciated, unlike standard debug methods, such as OBIC, LVP, TREM, etc., which require de-capsulation of the device and thinning the backside of the chip, with the setup of FIG.

4, the test is done without having to de-capsulate the chip. These and other features can be understood from the following examples.

Example I

Hot Spot Depth Determination at Single Chip Devices

Figure 6:
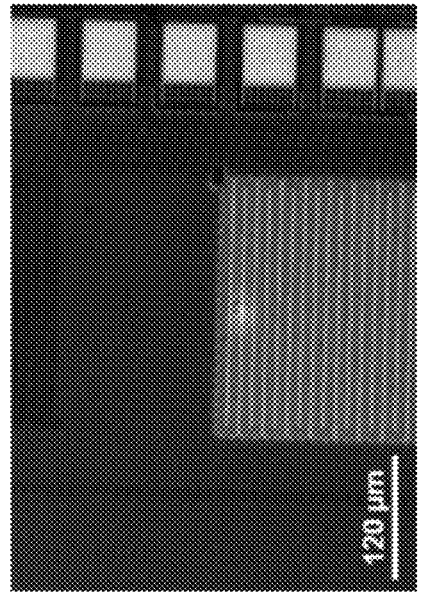
FIG. 6 is an image of the thermal intensity (Amplitude) overlaid over a topography image, showing the heat generated by the artificially generated defect (reference heat source) of the sample shown in FIG. 5.

The method of LIT can be used to non-destructively determine the hot spot position inside of a fully packaged single chip device providing a better alignment for the following physical failure analysis steps. The relationship between hot spot depth, applied lock-in frequency and resulting phase shift was investigated using test structures with defined point heat sources. The test structures were made using single chip device containing a meander of copper lines. The meander was locally modified by Focused Ion Beam technique (FIB), as shown in the upper part of FIG. 5 to generate well-defined local heat sources. After the creation of the local high resistance area the single chip device was measured by LIT with a supply voltage of 1.2 V and a lock-in frequency of 5 Hz creating a local heat source with a dissipation power of 14 mW. The resulting amplitude overlaid with the topography image is shown in FIG. 6. As a next step, the device was encapsulated with mould compound in order to create a material layer between the FIB made hot spots and the device surface. In this case the depth of the hot spots was known by the dimension of the device and the single chip and was determined at 950 µm.

Figure 7:
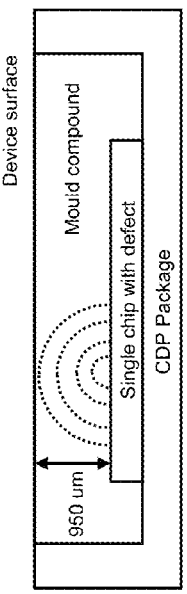
FIG. 7 is a simplified sketch of one device under test.

FIG. 7 shows a sketch of the investigated fully packaged test device. As shown in FIG. 7, a dual ceramic in-line package (DCIP) houses the single chip with the created defect. Mould compound was filled over the chip, to thickness of 950 µm over the top surface of the chip.

Figure 8:
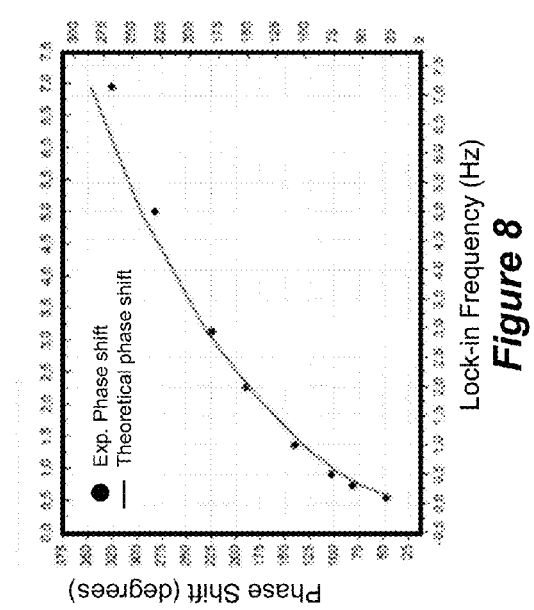
FIG. 8 is a plot of experimental and theoretical phase shift related to the applied lock-in frequency.

Based on the theory explained in the previous section, the DUT was investigated by the apparatus of FIG. 4 over a frequency range from 0.1 to 7 Hz and the resulting phase shift was measured. FIG. 8 shows the investigated relationship between applied lock-in frequency and resulting phase shift. The measured data points are plotted over the theoretical curve. It can be seen clearly that the trends matches the theoretical data for a lock-in frequency range of 0.1 to 3 Hz. In case of 5 and 7 Hz, a slight mismatch was obtained which can be explained by the low signal to noise ratio due to the higher damping of the thermal wave. This influence can be removed by a longer measuring time due to the fact that the stochastic noise of the detector is reduced by the square root of the measurement time.

The relationship between phase shift and lock-in frequency was determined experimentally for mold compound material with a good correlation to theoretical data. The obtained results are proving the potential of Lock-in Thermography investigations for 3D localization of thermal active structures or defects within fully package devices.

Incidentally, in the prior art, since a single lock-in frequency was used, the test results were provided as a single data point, such as those shown in FIG. 8. For example, if the lock-in frequency used was 2 Hz, then the output of the system would have been a single number, i.e., 177.5°. From this result, the single influences (correlation error, geometry influences, contact resistance, etc.) can not be separated, which is a necessary information for the investigation of complex 3D structures, such as SiP.

For the investigation of the internal heat propagation and the separation of different influences to the resulting phase shift the method of finite element modelling can be used simulating the lock-in process for a know device build up and a assumed defect position. As a first step, the steady state solution that considers the transient response is calculated using half of the assumed dissipation power in order to reach a stabile modulation within a few cycles. After reaching this "quasi—steady state," the sample is simulated with the pulsed excitation signal. Lock-in frequency, number of excitation periods and number of intermediate steps are chosen with reference to the real parameters. The thermal parameters of the encapsulated material (heat conductivity, heat capacity and density) are considered and the dissipation power is applied to the model ground and pulsed by various lock in frequencies. In addition, the time and power dissipation signals are saved in separate files, allowing the creation of the correlation functions and the reconstruction of the excitation signal. Two paths are created, where one is reading the temperature modulation over the surface and one over the thickness of the sample.

Example II

Defect Depth Determination at Stacked Die Devices

For 3D hot spot localization inside of stacked die integrated devices, e.g., a system-in-package, a second factor of influence has to be regarded. Thermal waves generated at the hot spot position have to propagate through different material layers, e.g., silicon, mould compound, die attach tape, etc., each having different thicknesses. As a consequence, depending on the axial hot spot position at different dies of the defective device, not only the distance to the device surface but also the thermal diffusion length is changing. Therefore, thermal waves generated at hot spots at lower dies inside of the stack have to pass additional material layers compared to thermal waves generated at hot spots which are close to the device surface. Like in the previous section regarding single chip devices, this behavior can be used for the determination of the hot spot depth by calculating the theoretical phase shift over a certain frequency range for different hot spot positions. Unlike the investigations of single chip devices, it is assumed that the hot spot is related to a specific die, which leads to the circumstance that a discrete model of the material system can be used. Therefore, at least to a first order, the total thermal diffusion length is the summation of the single thermal diffusion length of each material layer. Also, the total depth $z_{total}$ of the hot spot is the summation of the thicknesses $z_n$ of the single material layers.

$$\mu_{total} = \sum_{n=1}^{N} \mu_n = \sum_{n=1}^{N} \sqrt{\frac{2\lambda_n}{c_{p,n}\rho_n 2\pi f_{lock-in}}} \quad (4)$$

$$z_{total} = \sum_{n=1}^{N} z_n \quad (5)$$

This comparison shows for which assumed hot spot depth a match between experimental and theoretical data is given, which identifies the defective die inside the stack. This, however, does not take into account interference effects, nonlinearity, etc. To investigate this relationship on stacked die level, a test sample with a defined point heat source is necessary where the phase shift change in relation to additional material layers can be investigated stepwise. For this, stacked die test device was made, as shown in FIGS. 9A-9D. Point heat sources were generated again by FIB modification of single test chips with metal meander lines, illustrated in FIG. 9A. The resulting dissipation power was measured at 2.5 mW (0.5 V, 5 mA).

For the finite element simulation of the heat transfer through a stacked die sample the Lock-in process simulation is more complex using a 2D/3-D thermal model. The used stack materials (silicon, stacked die glue, mould compound, copper) and their thermal parameters are applied. Assuming different heat sources at different lateral and vertical positions inside of the material stack and correlate the resulting theoretical phase shifts for various lock in frequencies to the experimental data identifies the defect position.

Figure 9A:
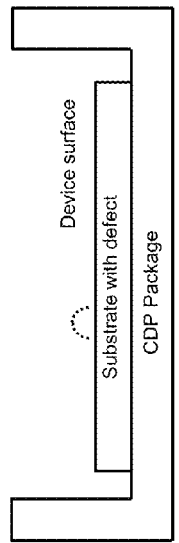
FIG. 9A-9D are sketches of the experimental setup.
Figure 9B:
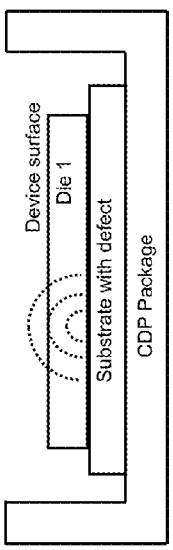
Figure 9C:
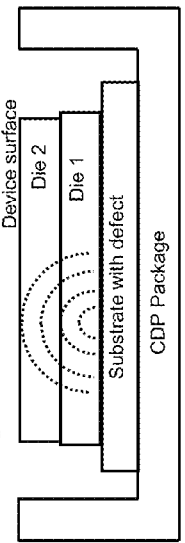
Figure 9D:
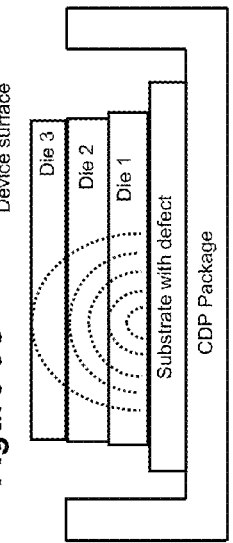

As a first step, the phase shift related to the applied lock-in frequency was determined, which can be used as a reference of a defect located at the device surface. As a next step, a bare silicon die with a thickness of 185 µm was attached at the surface of the prepared test chip using a die attach tape of 15 µm thickness, as shown in FIG. 9B. As a first approximation the thermal properties of the die attach tape can be seen similar to mold compound. Therefore, the additional die attached layer is responsible for a higher resulting phase shift. The bare silicon chip should not contribute significantly to the change of the phase shift, because it is transparent for IR light and the thermal conductivity is much higher. This procedure was applied two more times, creating finally a stacked die device with three dies above the generated heat source structure, as shown in FIGS. 9C and 9D.

Figure 10:
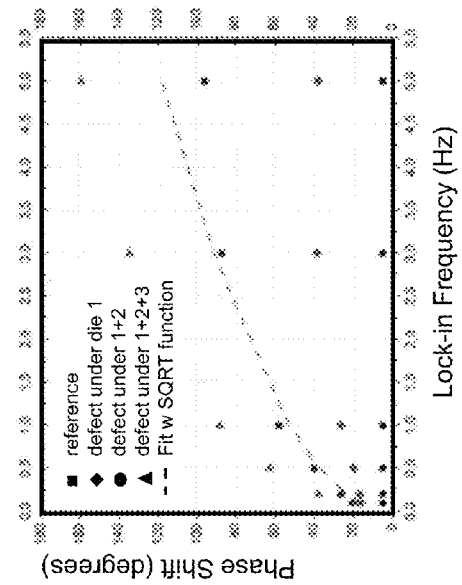
FIG. 10 is a plot of the experimental results of the investigated stacked device with different number of dies (DUT as shown in FIG. 9A-9D).

The experimental results of this investigation can be seen in FIG. 10. In addition, a square root fit is plotted (dashed line) in order to compare the slope of the experimental phase shift to the theoretical one. The plotted black rectangles are data points for measuring the defective die alone, as in FIG. 9A. Due to the fact that the defect is located at the device surface, the phase shift is independent of the applied lock-in frequency, which is proclaimed by the theory. Therefore, the defect depth z is zero, which results in a phase shift of 0° over all applied lock-in frequencies. In case of the attachment of a die above the defect area, the typical dependency of the phase shift to the lock-in frequency can be detected, as shown by the plotted rhombs. The further addition of dies (die 2 plotted as circles and die 3 plotted as triangle) leads to an ongoing increase of the resulting phase shift due to the additional material (both die and die attach tape) which has to be penetrated by the thermal wave.

By comparing the resulting phase shifts for different die numbers at the same frequency it can be seen that an additional die layer of 185 µm silicon and die attach tape of 15 µm leads to a phase shift increase between 40-60°. The experimental results of the phase shift under die 1+2 provide a good match with a theoretical phase shift for a frequency range of 0.1 to 3.

Example III

Time-Resolved Thermal Response

Figure 11:
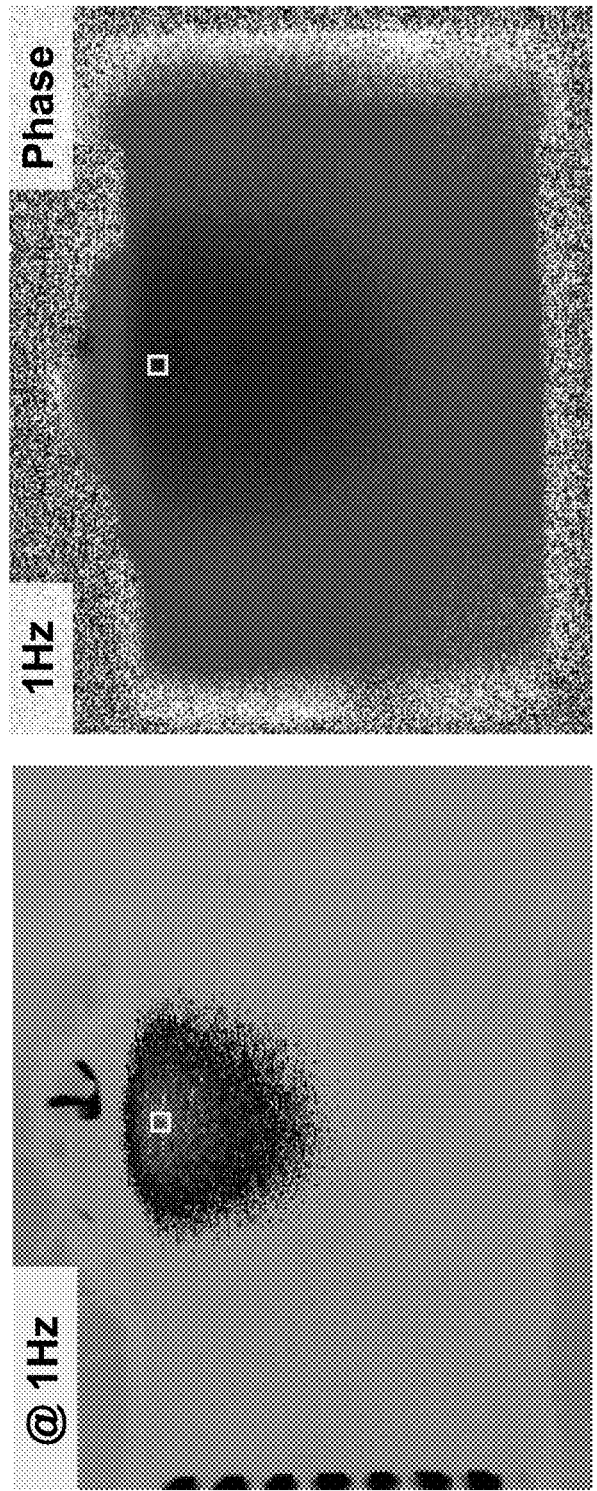

One disadvantage of traditional phase vs. frequency method is the long analysis time required. Measuring the phase across a full DUT with sufficient SNR may take several minutes (up to hours for high lock-in frequencies at thick, low-power samples). FIGS. 11A & 11B show a typical lock-in results, measured at $f_{lock-in}$=1 Hz and $V_{lock-in}$=1.2V with time of acquisition=15 minutes, with 11A being the amplitude result/image as an overlay on top of a topography image which is the basis for the localization of such a defect in x & y. FIG. 11B is the phase results, representing the local thermal delay per pixel. Since the x,y localization of a heat-source can be obtained from 11A, the final 3D analysis is reduced to the determination of the z-depth of the heat-source which only requires the phase value, measured right on top of the targeted heat-source. Therefore, taking measurement of the entire field of view, as shown in FIG. 11B for all required lock-in frequencies elongates the process and provides no additional benefit. Therefore, according to embodiments of the invention, the field of view of the camera is reduced, so that only a small area around the center of the hot spot is measured, as shown by the squares in FIGS. 11A and 11B. For example, according to one embodiment, the time-resolved thermal response analysis is based on measuring the necessary waveform by acquiring data in a very small window (e.g. 16×16 pixels, as illustrated by the yellow box in FIG. 11A, or even a single pixel) with much increased camera operation speed. During the data acquisition, the software can calculate the mean values across the small window or a subset (even smaller region) only covering the very center of the hot-spot at real time and averages the data, synchronized to the excitation (lock-in) frequency to generate the time-resolved thermal waveform (examples of such waveform are shown in FIGS. 12 and 13).

This process substantially increases the acquisition speed, since the SNR is based on the overall number of data points being averaged. By calculating the mean across the small window, the SNR per frame (captured image) can be increased by the number of pixels being included (e.g. 8×8=64). Additionally, the camera performs faster with reduced field of view (FOV), further increasing the acquisition by another 5 to 10 times (e.g. assuming 8). Compared to the pixel-wise lock-in where only one phase value per pixel is stored (averaged), the reconstruction of a time-resolved waveform requires to average the incoming data separately, regarding their time of acquisition with respect to the excitation (lock-in) period. Assuming a targeted time resolution of $1/40^{th}$ of the utilized excitation (lock-in) period, this would reduce the SNR time-resolved data point by 40×, since the acquired data has to be split evenly across all time slots. With the used numbers, this would result in an overall speed increase of about 12.8.

FIG. 12 shows time-resolved waveform results at full frame mode (100 Hz), all measured with $V_{lockin}$=1.2V, time of acquisition=40 sec, for different lock-in frequencies, showing clearly differently shaped waveforms. FIG. 13 shows time-resolved waveform results all measured with $V_{lockin}$=1.2V, time of acquisition=40 sec. These were measured by use of differently sized pixel arrays, allowing 2.61 times higher camera acquisition frame rate for the upper plot, showing much improved SNR. Setting a certain SNR target, this allows to clearly reduce the necessary acquisition time. Unlike the single data-point result of the prior art, using time-resolved waveform provides more information about the heat propagation within the device. That is, the time resolved waveform is obtained by plotting the thermal response of the device over time. This measurement is repeated for different lock-in frequencies. The shape of the time-resolved waveform obtained in different lock-in frequencies can be analyzed to determine the heat source's depth. For example, the waveform can be cross-correlated to various functions, such as sine function, saw-tooth function, shark-fine function, etc. The waveform can also be correlated to a calibration data or to a library of waveforms. Cross-correlating the time-resolved waveform provides further depth information in addition to the phase shift.

According to one embodiment, the initial image is taken using all of the pixels of the camera, e.g., 640×512 pixels of the sensor, e.g., InSb detector, as shown in FIG. 11A. The image is projected on the monitor (425 in FIG. 4) and the user is provided with a cursor to designate the location of the hot spot in x and y. The user may optionally also be provided with the ability to designate the size of the reduced field of view, e.g., select 16×16 pixels FOV. When the user initiates the testing sequence, data is collected only from the designated field of view. For example, only the pixels corresponding to the 16×16 pixels are read at each cycle. That is, rather than reading all of the pixels, e.g., 640×512=327680 pixels, only 16×16=256 pixels are read at each cycle. Since the amount of data collected from the camera is reduced by more than two orders of magnitude, the camera can be operated at a higher frame rate during the measurement process, thereby providing more data points for the averaging process. As another option, an IR sensor having a single pixel can be used.

Another way to implement the reduced field of view imaging is by what's generally called on-chip binning. When on-chip binning is activated, the data from neighboring pixels are collected into a single data point. For example, if a 2×2 binning is activated, then the values of four neighboring pixels are added to generate a single readout. In this way, the camera can be operated at faster readout speeds and improved signal to noise ratios, albeit at the expense of reduced spatial resolution. On the other hand, since the spatial location of the hotspot has already been determined, the reduced spatial resolution of the binning process is irrelevant as the measurement is used only to determine the depth, not the spatial location.

FIG. 14 shows another time-resolved thermal response measurement, also showing the used lock-in voltage and a sin function, plotted for the delay yielding highest cross-correlation between the sin function and the thermal waveform. The cross-correlation allows to measure the thermal time delay $\Delta\phi_{sin}$ (measured between the rising edge of the lock-in voltage and the zero-point of the sin function) with higher accuracy compared to measuring at 50% of the temperature signal swing. Furthermore, the cross-correlation value (number between 0 and 1, indicating how similar the two correlated functions/curves are; 0=uncorrelated, 1=identical) can be used as a second result, increasing the accuracy and reliability of the defect depth measurement.

Figure 15:
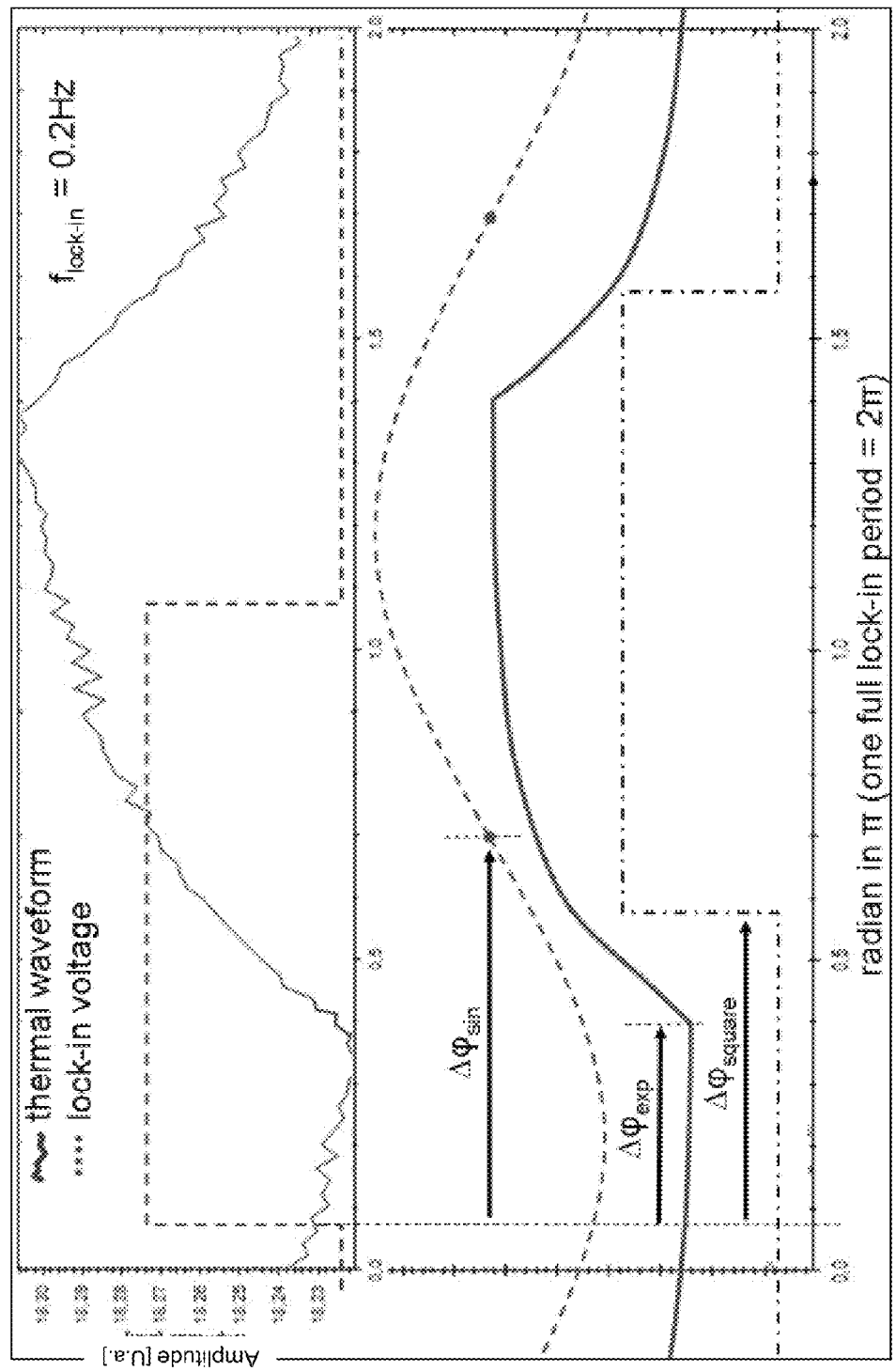
FIG. 15 shows a time-resolved thermal response measured at 0.2 Hz (see FIG. 12) superimposed to the lock-in voltage, in comparison to different potential functions used for cross-correlation. Shown are a sin-a exponential charging and discharging- and a square-function, all resulting in different $\Delta\phi$ and cross-correlation values.

Using multiple predefined functions for cross-correlation allows to analyze the shape of the thermal waveform in a quantified and reproducible way. The idea is illustrated in FIG. 15, where a thermal waveform with non-sin like shape is shown in comparison to the lock-in voltage and three different correlation functions. All three correlation function will deliver different delay values whereby the sin (dashed green) and the exponential charging/discharging curve (exp; red solid line) will have a clearly higher cross-correlation value compared to the square wave. All these values (results) can be used to compare to theoretically or experimentally derived reference data to yield the defect depth localization with sufficient accuracy (e.g. determination of defective layer out of a die-stack in a package).

As can be understood from the above, embodiments of this invention enable the use of Lock-in Thermography for quantitative and non destructive 3D localization of hot spots i.e. generated by electrical structures or defects inside of electronic devices. The relationship between the applied lock-in frequency and the phase shift was determined based on the physical principles of thermal waves. This was done for the case where a hot spot is buried under a single material layer of unknown thickness and for the case of a hot spot buried under an unknown number of dies inside of a stacked die device. It was shown that buried hot spots even under a thick layer of mould compound can be localized in all three dimensions.

Furthermore, different die layers of system in package architectures could be measured showing significant phase shift differences, allowing the exact determination of the defective die through the package. Due to the non-homogeneous material stack of stacked dies with complex thermal properties it becomes necessary to acquire multiple LIT results at different lock-in frequencies. The method of acquiring and analyzing these results for hot spot depth calculation is enabled by embodiments of the invention.

Embodiments of the invention also enable the use of the time-resolved thermal response for more precise hot spot depth analysis, based on a point measurement. This allows decreasing the necessary measurement time substantially. Furthermore, it enables a more detailed data analysis of the shape of the acquired thermal waveform in addition to the thermal time delay.

It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein.

The present invention has been described in relation to particular examples, which are intended in all respects to be illustrative rather than restrictive. Those skilled in the art will appreciate that many different combinations of hardware, software, and firmware will be suitable for practicing the present invention. Moreover, other implementations of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for detecting the location of buried heat sources using lock-in-thermography (LIT) system, comprising:
    placing a device under test (DUT) on a test system;
    applying electrical excitation signals at a first lock-in frequency to the DUT;
    while the excitation signals are applied to the DUT, imaging the DUT using an infrared (IR) camera;
    detecting lateral temperature distribution on a surface of the sample to thereby locate the heat-source laterally;
    repeatedly applying electrical excitation signals at multiple different lock-in frequencies to the DUT;
    plotting thermal response of the DUT to thereby obtain time-resolved waveforms for the multiple different lock-in frequencies:
    detecting resulting phase shifts between the electrical excitation signal and the thermal response for each of the lock-in frequencies; and,
    analyzing the resulting phase shifts as a function of each of the applied lock-in frequencies to thereby obtain depth location of the electrical active heat source.

2. The method of claim 1, further comprising analyzing the slope of the time-resolved waveforms to thereby improve z-resolution and measurement reliability.

3. The method of claim 1, further comprising calculating depth related phase shift to frequency behavior by analytical solution of the thermal wave propagation; and,
    correlating the calculated depth related phase shift frequency behavior to the measured phase shift to identify the depth of the heat source.

4. The method of claim 1, further comprising calculating depth-related phase shift to frequency behavior by finite element modeling of thermal wave propagation;
correlating the calculated depth-related phase shift frequency behavior to the measured phase shifts to identify the depth of the heat source.

5. The method of claim 1, wherein applying electrical excitation signal comprises obtaining the test signal from an external source and synchronizing the IR camera to the signal from the external source.

6. The method of claim 1, further comprising:
superimposing a plot of lock-in voltage of the selected lock-in frequency over the time-resolved waveforms; and,
fitting a potential function used for cross-correlation to the plot of the time-resolved thermal response.

7. The method of claim 6, wherein the plotting of the time-resolved thermal response is performed for one full lock-in period.

8. The method of claim 6, wherein fitting a potential functions comprises fitting a sine function.

9. The method of claim 8, further comprising calculating a thermal time delay from a rising edge of the lock-in voltage and a zero-point of the sine function.

10. The method of claim 9, further comprising calculating cross-correlation value comprising a number between 0 and 1, indicating how similar the sine functions and the plot of time-resolved thermal response are.

11. The method of claim 1, and further for each of the lock-in frequencies performing the steps comprising:
superimposing a plot of lock-in voltage of a selected lock-in frequency over the time-resolved waveforms; and,
fitting a potential function used for cross-correlation to the plot of the time-resolved thermal response.

12. The method of claim 1, further comprising:
fitting a plurality of different potential function used for cross-correlation to the plot of the time-resolved thermal response onto one of the time-resolved waveforms; and,
determining a phase shift from each of the potential functions.

13. The method of claim 12, further comprising comparing each of the phase shifts to theoretically or experimentally derived reference data to yield a defect depth localization.

14. The method of claim 1, further comprising, after locating the heat-source laterally, performing on-chip binning to reduce the field of view of the IR camera.

15. The method of claim 1, further comprising, after locating the heat-source laterally, reducing the operational area of the IR camera by adding values of neighboring pixels to generate summation data points, and reading only the summation data points.

16. The method of claim 1, further comprising reducing the field of view of the IR camera after detecting lateral temperature distribution but prior to detecting resulting phase shifts.

17. The method of claim 16, wherein reducing the field of view of the IR camera comprises using a single pixel IR sensor.

18. The method of claim 16, wherein reducing the field of view of the IR camera comprises providing a cursor to an operator to designate the location of the heat-source laterally in x and y.

19. The method of claim 18, further comprising providing the user with the ability to designate size of the reduced field of view.

20. The method of claim 16, further comprising after reducing the field of view, operating the IR camera at a higher frame rate.

* * * * *